United States Patent [19]

Piacquadio

[11] Patent Number: 5,443,824
[45] Date of Patent: Aug. 22, 1995

[54] TOPICAL THALIDOMIDE COMPOSITIONS FOR SURFACE OR MUCOSAL WOUNDS, ULCERATIONS, AND LESIONS

[76] Inventor: Daniel J. Piacquadio, 9723 Saskatchewan, San Diego, Calif. 92129

[21] Appl. No.: 212,520

[22] Filed: Mar. 14, 1994

[51] Int. Cl.$^6$ ............................................. A61K 31/445
[52] U.S. Cl. ................................. 424/78.02; 514/323
[58] Field of Search ........................... 514/772.4, 323; 424/78.02

[56] References Cited

U.S. PATENT DOCUMENTS

| | | | |
|---|---|---|---|
| 2,830,991 | 4/1958 | Keller | 260/281 |
| 2,957,872 | 10/1960 | Nuebner | 260/247.2 |
| 3,025,300 | 3/1962 | Huebner | 260/294 |
| 3,091,568 | 5/1963 | Oscar | 167/55 |
| 3,563,986 | 2/1971 | Frankus et al. | 260/247.1 |
| 3,625,946 | 12/1971 | Koch et al. | 260/281 |
| 3,951,985 | 4/1976 | Graudums et al. | 260/293.57 |
| 4,053,615 | 10/1977 | Boyle et al. | 424/267 |
| 4,067,085 | 1/1978 | Graudums et al. | 424/267 |
| 4,120,649 | 10/1978 | Schechter | 8/94.11 |
| 4,461,619 | 7/1984 | Hendry et al. | 434/295 |
| 4,882,048 | 11/1989 | Blaschke et al. | 210/198.2 |
| 4,996,193 | 2/1991 | Hewitt et al. | 514/11 |
| 5,057,427 | 10/1991 | Wald et al. | 435/280 |
| 5,077,217 | 12/1991 | Matson et al. | 435/280 |
| 5,079,152 | 1/1992 | Benkovic et al. | 435/125 |
| 5,104,899 | 4/1992 | Young et al. | 514/646 |
| 5,114,715 | 5/1992 | Young et al. | 424/400 |
| 5,120,720 | 6/1992 | Pitha et al. | 514/58 |
| 5,134,127 | 7/1992 | Stella et al. | 514/58 |
| 5,135,915 | 8/1992 | Czarniecki et al. | 514/21 |

OTHER PUBLICATIONS

Journal of Infectious Diseases Sampaio et al. 1993.
Sheskin et al 81:290959 1981 Dermatologica.
Shannon et al Zeki Rev Mar. 1992 63(1).
Eisenbud et al 87:487541 1987 Oral Leery Oral Path. Med.
Soto et al. Rev. Med U. S. Navidad 1988.
Proencca Rev. Paul Med 1989 167(1).
Grinskan et al. Amer. Acad. Derm. 1989.
Hawkins, The Lancet, vol. 339, p. 1057, Apr. 25, 1992.
Bessis et al., The Lancet, vol. 339, pp. 549–550, Feb. 29, 1992.
Burrows et al., British Journal of Detmatology, (1991) 125, 62–67.
Heney, et al., British Journal of Haematology, 1991, 78, 23–27.
Sampaio, et al., J. Exp. Med., vol. 173, Mar. 1991, 699–703.
Gehanno, et al., Ann. Oto–Laryng., 1990, 107, 311–313.
Lo, et al, International Journal of Dermatology, Oct. 1989, vol. 28, No. 8 pp. 497–507.
Günzler, Medical Hypotheses (1989) 30, 105–109.
Crain, et al., Autoimmunity (1989) 2, 197–202.
Schmahl, et al., Arch Toxicol, (1988) 62:200–204.
Heney, et al., Pharmacother (1990) 44, 199–204.

*Primary Examiner*—Thurman K. Page
*Assistant Examiner*—Peter F. Kulkosky
*Attorney, Agent, or Firm*—Zarley, McKee, Thomte, Voorhees, & Sease

[57] ABSTRACT

Surface wounds, ulcerations and lesions are treated with a solubilized topical composition containing as its active thalidomide or a pro drug, analog or biologically active salt form thereof.

14 Claims, 3 Drawing Sheets

TOPICAL THALIDOMIDE COMPOSITIONS FOR SURFACE OR MUCOSAL WOUNDS, ULCERATIONS, AND LESIONS

BACKGROUND OF THE INVENTION

The present invention relates to a new use for a known compound, thalidomide. Thalidomide has been known as a tranquilizer since the late 1950's. The compound thalidomide was patented in Keller, U.S. Pat. 2,830,991 issued Apr. 15, 1958. It has the chemical name 3-phthalimido-piperidine dione 2,6. Thalidomide is a derivative of glutamic acid.

As is well known, it was widely used in the early 1960's as a tranquilizer in Europe, although never approved for use in the United States. When it was discovered that even small amounts of thalidomide when taken by pregnant women caused birth defects, the drug was rapidly withdrawn from the market. As a result, thalidomide was never approved for use in the United States. Since that period in the early 1960's researchers have found that thalidomide is useful in treating inflammation associated with severe cases of erythema nodosum leprosum (ENL) leprosy. There is also literature indicating that the drug is useful in treating inflammatory processes associated with for example Lupus, see Lo, et al., treatment of discoid Lupus erythematosus, *International Journal of Dermatology*, October 1989 Vol. 29, No. 8, p. 497–507.

At this point it is beyond question that thalidomide when taken by pregnant women is a teratogen; however, the fact remains that sufficient scientific evidence exists to merit its investigation for uses in environments in which it will not have the opportunity to function as a teratogenic agent. For example, thalidomide is now widely used in treatment of leprosy in situations where there is no risk to females of child bearing potential.

In summary, thalidomide is known to have sedative and hypnotic effects and to be useful in treating Lupus and leprosy. Care must be taken, however, when thalidomide is used, to avoid systemic use in females of child bearing potential.

Recognizing this limitation of thalidomide, but also the potential value of the drug, a research project was begun to determine whether or not a technique could be developed to take advantage of uses of thalidomide without significant risk of its teratogenic effects. In this regard investigations were commenced into possible uses of thalidomide as a topical treatment, the theory being that if used topically as opposed to systemically, advantages of the drug could be used without the disadvantages.

In commencing such investigations the research was compounded in difficulty by the fact that thalidomide, its pro drugs and analogues are difficultly soluble at best. This lack of solubility creates special formulation problems for topicals, since an effective-topical composition must have satisfactory percutaneous absorption levels in order to be effective.

Accordingly, it is the primary object of the present invention to prepare effective solubilized topical compositions of thalidomide useful for treating skin ulcerations and lesions.

Another objective of the present invention is to provide an oral solution or mucosal irrigant and skin ointment pharmaceutical compositions effective for treating skin and mucosal ulcerations and lesions, which compositions contain as their active solubilized thalidomide.

Another objective of the present invention is to provide thalidomide in a delivery system which can be used for topical treatment without causing adverse systemic effects.

The method and means of accomplishing each of the above objectives as well as others will become apparent from the detailed description of the invention which follows hereinafter.

SUMMARY OF THE INVENTION

Figure 1:
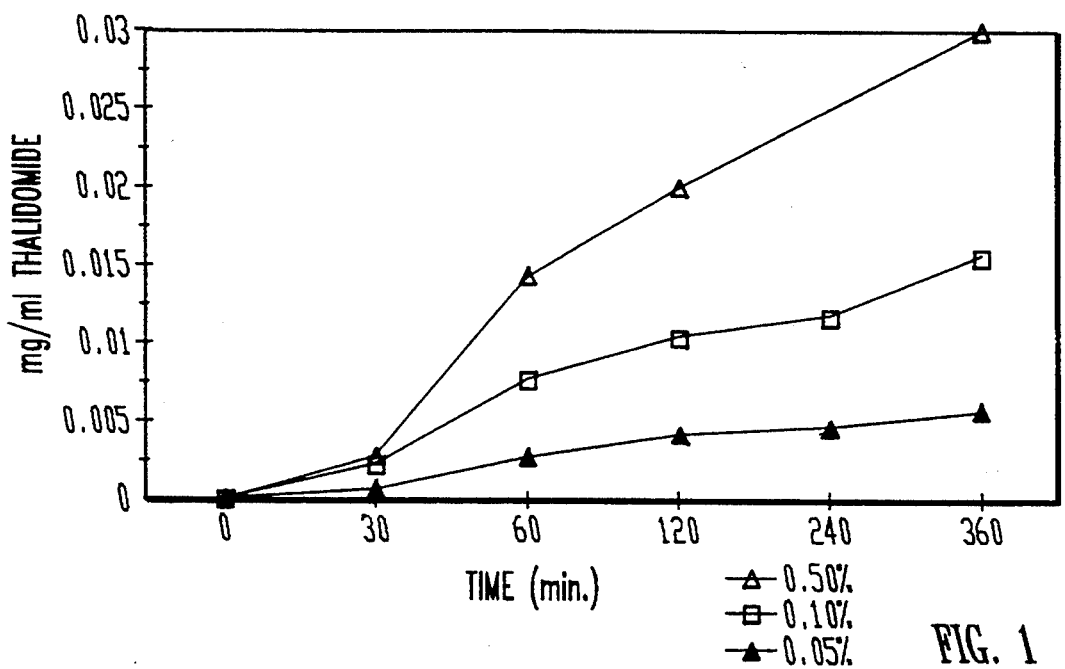
FIGS. 1-6 show results of cell diffusion studies of various thalidomide active levels through various membranes.

The invention relates to a method and composition for treating skin and mucosal ulcerations and lesions topically with thalidomide, its pro drugs and analogues. Topical treatment on a regular basis provides dramatically increased wound healing for skin ulcerations and lesions, and avoids the risk of systemic treatment with thalidomide. The compositions comprise thalidomide solubilized in polyethylene glycol, preferably of middle range molecular weight.

DETAILED DESCRIPTION OF THE INVENTION

The present invention relates to new uses for thalidomide, a known derivative of glutamic acid. Thalidomide has the formula:

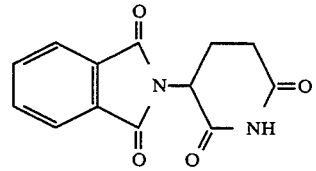

When the term "thalidomide" is used herein it is understood that it contemplates not only the compound itself but pro drugs which metabolize to the compound and analogues and biologically active salt forms thereof, as well as optical isomers which provide the same pharmaceutical result.

As earlier mentioned, thalidomide is a known effective sedative and hypnotic. The toxicity is also very low. The $LD_{50}$ (standard amount which causes death of 50% of the animals investigated) is so low that the $LD_{50}$ could not be established. Toxicity data on rats states it to be practically non-toxic with an oral dose of 10 g/kg.

This invention is predicated upon the discovery that thalidomide in topical compositions wherein the thalidomide is effectively solubilized so that it can be percutaneously absorbed and can be successfully used for treating skin ulcerations and lesions. It is particularly applicable for treating connective tissue diseases, inflammatory skin, mucosa and conjunctive disorders, disorders of keratinization, bullous skin diseases and other immune mediated diseases of the skin, mucosa and conjunctiva as well as leprosy, and such other similar infectious diseases.

The important point is that previously it was thought that thalidomide had to be used systemically or in combination with other actives to provide desired treatment effects. It had not, however, been discovered that thalidomide alone as the only active can be used, providing that it is used in a topical composition in which the thalidomide is effectively solubilized.

As earlier discussed, thalidomide is only difficultly soluble. It therefore becomes incumbent to find a suitable delivery system if it is to be effective in treating skin ulcerations and lesions such as those associated with the above-mentioned disease conditions.

With the above observations in mind, the solubility of thalidomide, racemic mixtures thereof, and both the D and the L isomers individually, were investigated in many solvents. The studies involved formation of saturated solutions by mixing 0.5 grams of thalidomide and 20 grams of solvent for at least 14 hours at room temperature (23° C.). The solutions were then centrifuged and filtered through 0.45 micromillimeter membranes of skin. Finally the clear samples were assayed using high performance liquid chromatography procedures. The percent thalidomide reported for each solvent was recorded. Care was taken to filter the warm sample with a syringe/filter membrane system which had been previously warmed in a 60° C. oven.

The following table shows the results of the above experiments:

TABLE 1

| Solvent | Saturated % w/w Thalidomide |
| --- | --- |
| Azone | 0.100 |
| Glycerin | 0.020 |
| Propylene Glycol | 0.082 |
| Polypropylene Glycol | 0.042 |
| 1,3 Butanedoil | 0.038 |
| Polyethylene Glycol E200 | 0.450 |
| Polysorbate 20 | 0.329 |
| Polyethylene Glycol E400 (RT) | 0.541 |
| Polyethylene Glycol E400 (52° C.) | 0.769 |
| Water | 0.006 |
| USP Alcohol | 0.062 |

Based upon the above data it can be seen that middle range molecular weight polyethylene glycol was the only satisfactory, and generally recognized as safe (GRAS) solvent that showed promise. Accordingly, further investigative results focused upon use of middle range molecular weight polyethylene glycol as the only suitable and safe solvent for thalidomide.

In accordance with the data above reported as well as other data it was discovered that polyethylene glycol, having a weight average molecular weight within the range of from about 200 to about 600 provided satisfactory solubilization levels of thalidomide to achieve topically effective results both in solutions and ointments.

In particular, satisfactory percutaneous absorption was shown with topical compositions that contain thalidomide as the active in a polyethylene glycol carrier such that the compound could be used for effective topical treatment of skin lesions and ulcers. With suitable daily topical application in accord with the process of this invention, most skin ulcers and lesions may be put into remission in short periods of time.

The topical composition should comprise from about 0.01% to about 30% by weight of thalidomide, and preferably from about 0.05% to about 10% by weight of thalidomide. The polyethylene glycol is polyethylene glycol that can be obtained from a wide variety of pharmaceutically acceptable sources. As earlier mentioned the polyethylene glycol that has a medium average molecular weight within the range of from about 200 to about 600 is preferred. Satisfactory results are achieved when the polyethylene glycol carrier is a blend of for example polyethylene glycol average molecular weight 200 and average molecular weight 400. If one desires an ointment rather than for example an oral or mucosal solution composition, the polyethylene glycol should be a blend and may contain some polyethylene glycol having for example an average weight of about 3350.

Generally where blends are employed for ointments the ratio of polyethylene glycol lower molecular weight to higher molecular weight (e.g. 3350) should be from 1:8 to 1:0.2, preferably from 1:0.5 to 1:2, most preferably 1:0.30. If only one polyethylene glycol is to be used, for example in a solution, it is preferred that it be polyethylene glycol 400 in view of the best solubilization characteristics in this weight (see Table 1).

Where a preferred ointment composition is used, the amount of polyethylene glycol 3350 should be at least 25% of polyethylene glycol blend.

In addition to the active thalidomide form and the polyethylene glycol pharmaceutical carrier, the composition may contain suitable preservatives, stabilizers, wetting, dissolving and sweetening agents as well as coloring, preservatives and fragrances. These minors are added in very small amounts and are conventionally known in pharmaceutical formulation work to enhance elegance. Generally they are added at ranges of from 0.01% to about 2% by weight.

The composition of the present invention is administered topically in dosages effective to provide the desired treatment enhancement condition. Generally this will be levels to provide about 100 milligrams to about 200 milligrams dosage per day. This would usually involve 3–6 topical applications per day.

The following examples are offered to illustrate but not limit the invention. Thus they are presented with the understanding that various formulation modifications as well as method of delivery modifications may be made and still be within the spirit of the invention.

EXAMPLES

Tests of percutaneous absorption for polyethylene glycol compositions containing thalidomide active within the ranges herein expressed were conducted using a modified Franz diffusion cell. Generally the technique of using a Franz diffusion cell is described in a catalogue number PA-1-85 of Crown Glass Company, Inc. entitled, "Systems For The Measurement Of Percutaneous Absorption". As another general reference one can also see Current Problems In Dermatology, Vol. 7, pp. 58–68 (Karger, Basel 1978) article by Dr. Thomas J. Franz describing the Franz diffusion cell, its theory and use. In the cell skin is mounted between the cell cap and the cell body. The dermos is bathed from below by a receptor fluid isotonic saline solution injected through a port provided for that purpose. The temperature is maintained at 37° by thermostatically-controlled water which enters a lower port of the water jacket surrounding the saline chamber that circulates out through the upper port. Effective transport of active across the skin and into the solution on the lower side is then measured.

Figure 3:
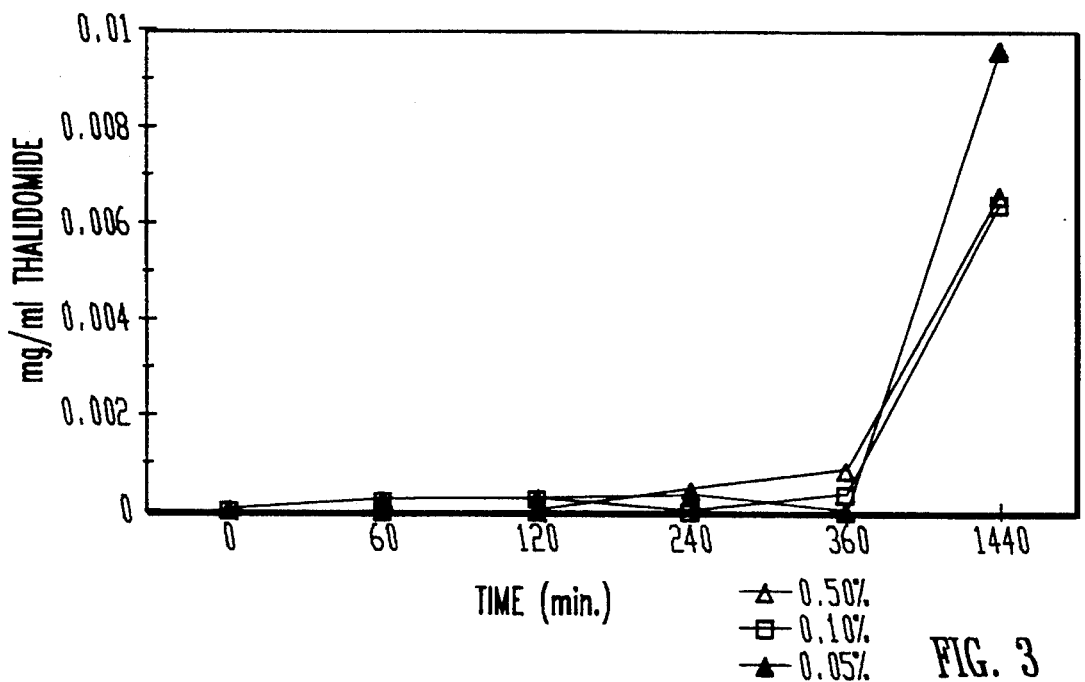
Figure 4:
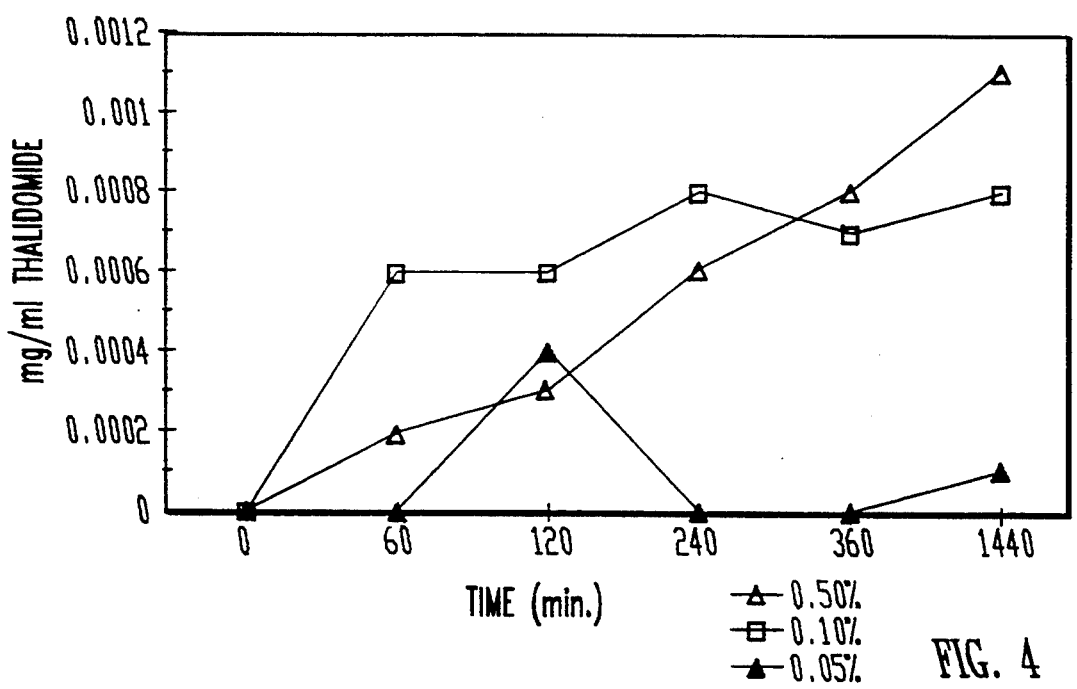
Figure 5:
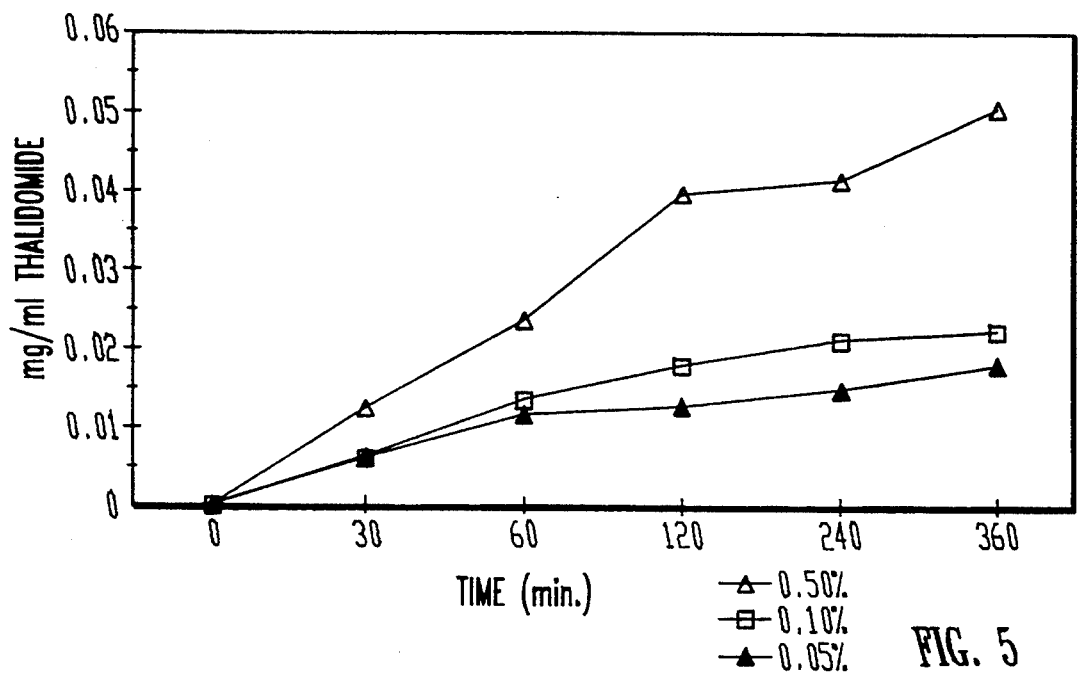
Figure 6:
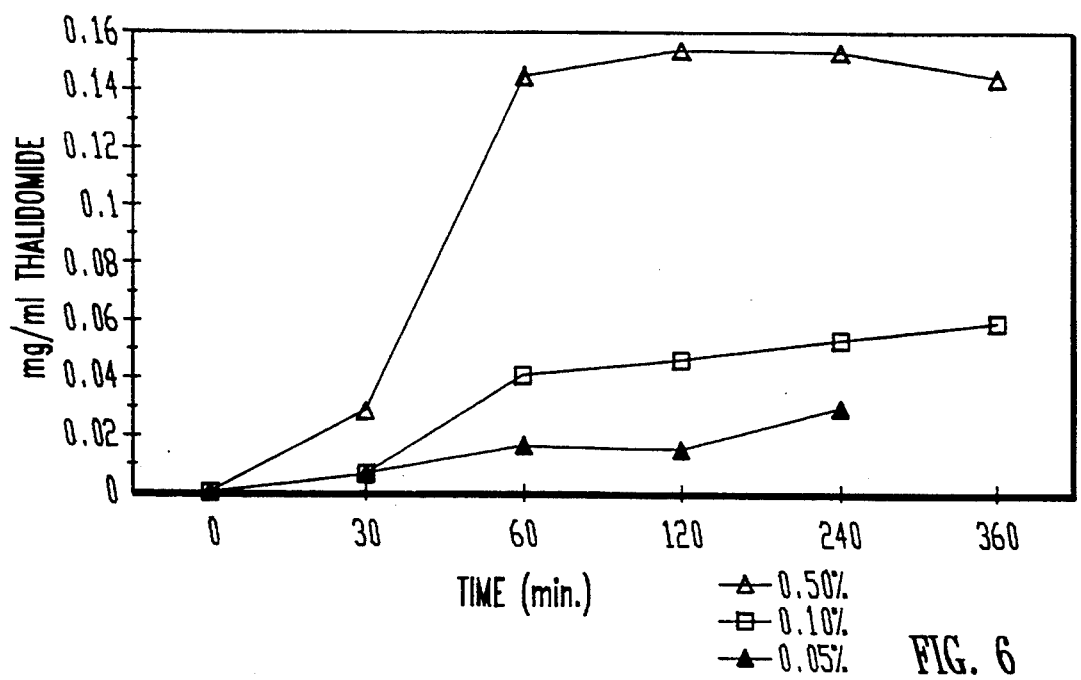

FIGS. 1–6 present diffusion transport results using the above-described technique. They demonstrate effective transport across the Franz diffusion cell for the various described thalidomide compositions. The membranes used were cellulose acetate/nitrate (FIG. 1–2); nude mouse skin (FIG. 3–4); nylon (FIG. 5–6). For the ointment the base was a PEG 400:PEG 3350 of 1:0.30. For the solution the base PEG 400.

Figure 2:
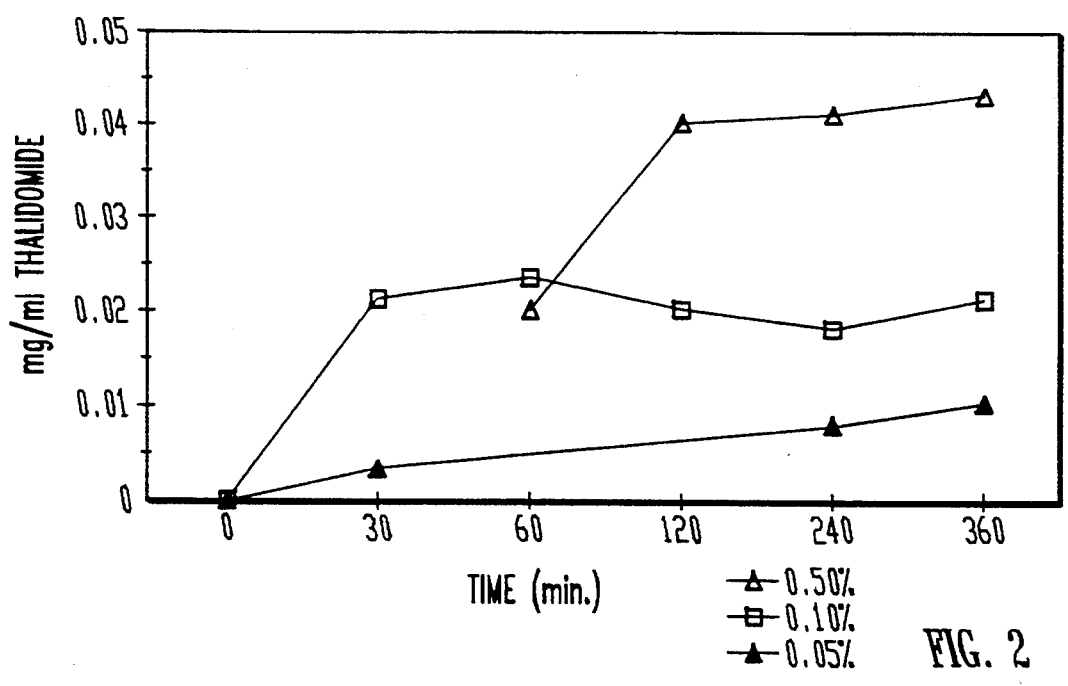

FIG. 1 shows cell diffusion studies for 0.50%, 0.10% and 0.05% thalidomide ointment preparations using a cellulose acetate and nitrate membrane. The results of this study demonstrate a concentration dependent dose response over time. FIG. 2 shows similar comparisons and results for a thalidomide solution. FIG. 3 shows the ointment cell diffusion test for nude mouse skin and indicates thalidomide will pass through nude mouse skin. FIG. 4 shows similar results for a solution. FIGS. 5 and 6 demonstrate dose response results for ointment and solution on a nylon membrane.

It can be seen from the above material that thalidomide in both solution and ointment compositions can be released through diffusion cell membranes. The data suggests that dose response criteria can be achieved.

Following the discoveries of the compatibility and solubility of thalidomide solutions in mid range molecular weight polyethylene glycol, pharmaceutical ointment compositions that comprise a blend of the polyethylene glycols 400 and 3350 at a ratio of 1:0.30 and 0.5% by weight. In addition the continued GRAS adhesive polymers. A patient was selected as one suffering from an aphthous ulcer in the mandibular buccal vestibule adjacent to the first right premolar. The lesion, an oval superficial erosion with a whitish base, measured approximately 3×6 mm in size. The lesion was notably painful and was surrounded by ill-defined erythema. A second lesion adjacent to the first was notable for an area of ill-defined erythema and tenderness but no frank lesion. Treatment was begun using QID (4×/day) applications with four doses being administered the first day to both sites. At the start of the second day of therapy the ulcer lesion was notably less painful and the surrounding erythema had essentially resolved. The lesion with erythema only was no longer present. The ulcer lesion was pain free by the next morning and had decreased in size by about 50%. The following morning, no significant mucosa change remained.

In observing this patient and comparing the patient with other patients suffering the similar condition, the following empirical observations can be made.

The rate of healing was improved by 30-50% compared to a typical episode for the patient. In addition to a decrease in healing time, the symptoms associated with the ulcer also improved more quickly. The response of the second lesion suggests that early intervention may halt the progression of the disease in its early stages; however, the true nature of this second lesion cannot be firmly established.

This clinical experience is consistent with the observations of thalidomide solubility, thalidomide percutaneous absorption and indicates a significant treatment effect advantage over more conventional treatments of such an aphthous ulcer which would normally be a regimen of topical/systemic antibiotics and antifungal agents (e.g. tetracycline, clindamycin, ketaconazole), nonsteroidal anti-inflammatory agents, and topical anesthetics for symptomatic relief. Colchicine has been found somewhat beneficial. Steroids are used with some success, although their use holds a risk of opportunistic infection due to reduced immunologic defenses.

It therefore can be seen that applicant has discovered certain unique characteristics of thalidomide, which take advantage of low toxicity of thalidomide, and which avoid the teratogen effect of thalidomide, and which provide a composition effective against skin and mucosal ulcers and lesions. The drug is administered at site specific locations, rather than systemically. This allows smaller doses, and less patient risk than the systemic route.

It should be mentioned that while the above description has been given with regard to topical application, application may also be intralesionally accomplished. Likewise the composition may be thalidomide itself, or pro drugs or analogues of thalidomide or of a racemic mixture or either the D or the L form. Also minor dosage and formulation modifications of the composition and the ranges expressed herein may be made and still come within the scope and spirit of the present invention.

What is claimed is:

1. A method of treating skin and mucosal ulcerations and lesions, comprising:
   topically applying to an affected skin area a small but treatment effective amount of a thalidomide composition comprising, from about 0.01% to about 30% by weight thalidomide and medium range molecular weight polymers of polyethylene glycol having an average molecular weight of from about 200 to about 600 average molecular weight.

2. The method of claim 1 wherein the thalidomide is from about 5% to about 10% by weight of said composition.

3. The method of claim 1 wherein the thalidomide is in a topical composition in which substantial amounts of the thalidomide are soluble.

4. The method of claim 1 wherein the polyethylene glycol is a blend of polyethylene glycol average molecular weight 200 and polyethylene glycol 400.

5. The method of claim 4 wherein the polyethylene glycol is polyethylene glycol average molecular weight 400.

6. The method of claim 1 wherein the polyethylene glycol is heated to above room temperature before addition of the thalidomide.

7. The method of claim 1 wherein the topical composition is an oral mucosal solution.

8. The method of claim 1 wherein the topical composition is an ointment, cream or gel.

9. A topical composition for treating skin ulcerations and lesions, comprising:
   from about 0.01% by weight to about 30% by weight of thalidomide solubilized in a polyethylene glycol carrier wherein the polyethylene glycol carrier has an average molecular weight within the range of from about 200 to about 600.

10. The composition of claim 9 wherein the carrier is a blend of polyethylene glycol of average molecular weight 200 and polyethylene glycol average molecular weight 400.

11. The composition of claim 9 wherein the composition is an oral mucosal solution.

12. The composition of claim 9 wherein the composition is an ointment, cream or gel.

13. The composition of claim 9 which comprises a blend of polyethylene glycol average molecular weight 400 and polyethylene glycol average molecular weight 3350.

14. A method of treating skin and mucosal ulcerations and lesions, comprising:
   topically applying to an affected skin area a small but treatment effective amount of a solubilized thalidomide composition containing from about 0.01% by weight to about 30% by weight thalidomide in a pharmaceutically acceptable carrier.

* * * * *